(12) United States Patent
Alan

(10) Patent No.: US 10,426,937 B2
(45) Date of Patent: Oct. 1, 2019

(54) BI-PHASE FLUID SURGE SUPPRESSOR DEVICE

(71) Applicant: INTEGRA LIFESCIENCES SWITZERLAND SÀRL, Le Locle (CH)

(72) Inventor: Dextradeur Alan, Franklin, MA (US)

(73) Assignee: INTEGRA LIFESCIENCES SWITZERLAND SÀRL, Le Locle (CH)

( * ) Notice: Subject to any disclaimer, the term of this patent is extended or adjusted under 35 U.S.C. 154(b) by 213 days.

(21) Appl. No.: 15/137,687

(22) Filed: Apr. 25, 2016

(65) Prior Publication Data

US 2016/0235951 A1    Aug. 18, 2016

Related U.S. Application Data

(63) Continuation of application No. 13/799,281, filed on Mar. 13, 2013, now abandoned.

(51) Int. Cl.
| | | |
|---|---|---|
| *A61M 27/00* | (2006.01) | |
| *F16K 17/12* | (2006.01) | |
| *A61M 39/24* | (2006.01) | |
| *A61M 39/22* | (2006.01) | |

(52) U.S. Cl.
CPC .......... *A61M 27/006* (2013.01); *A61M 39/24* (2013.01); *F16K 17/12* (2013.01); *A61M 2039/226* (2013.01); *A61M 2039/248* (2013.01)

(58) Field of Classification Search
CPC ...... A61M 2039/226; A61M 2039/248; A61M 39/24; A61M 27/006

USPC ........................................................ 604/9, 10
See application file for complete search history.

(56) References Cited

U.S. PATENT DOCUMENTS

| | | | |
|---|---|---|---|
| 3,889,687 A * | 6/1975 | Harris ................ | A61M 27/006 137/38 |
| 5,368,556 A | 11/1994 | Lecuyer | |
| 5,634,894 A | 6/1997 | Magram | |
| 6,126,628 A | 10/2000 | Nissels | |
| 6,146,352 A | 11/2000 | Bonnal | |
| 2006/0089589 A1 | 4/2006 | Portnoy | |

FOREIGN PATENT DOCUMENTS

| | | |
|---|---|---|
| DE | 19535637 A1 | 3/1997 |
| EP | 2253352 A1 | 11/2010 |

\* cited by examiner

*Primary Examiner* — Kai H Weng
(74) *Attorney, Agent, or Firm* — Troutman Sanders LLP

(57) ABSTRACT

A siphon guard includes a housing having an inlet and an outlet. A primary flow path is disposed within the housing and is in fluid communication with the inlet and the outlet. A secondary flow path is disposed within the housing and is in fluid communication with the inlet and the outlet. The secondary flow path has a higher resistance to fluid flow than the primary path. A valve is disposed within the primary flow path. The valve has a valve seat and a first ball and a second ball. The first ball is movable by gravity between a valve closed position, where the first ball is in contact with the valve seat, and a valve open position, where the first ball is spaced from the valve seat. The first ball is disposed between the second ball and the valve seat. The second ball is movable by gravity between a valve closed position and a valve opened position.

11 Claims, 4 Drawing Sheets

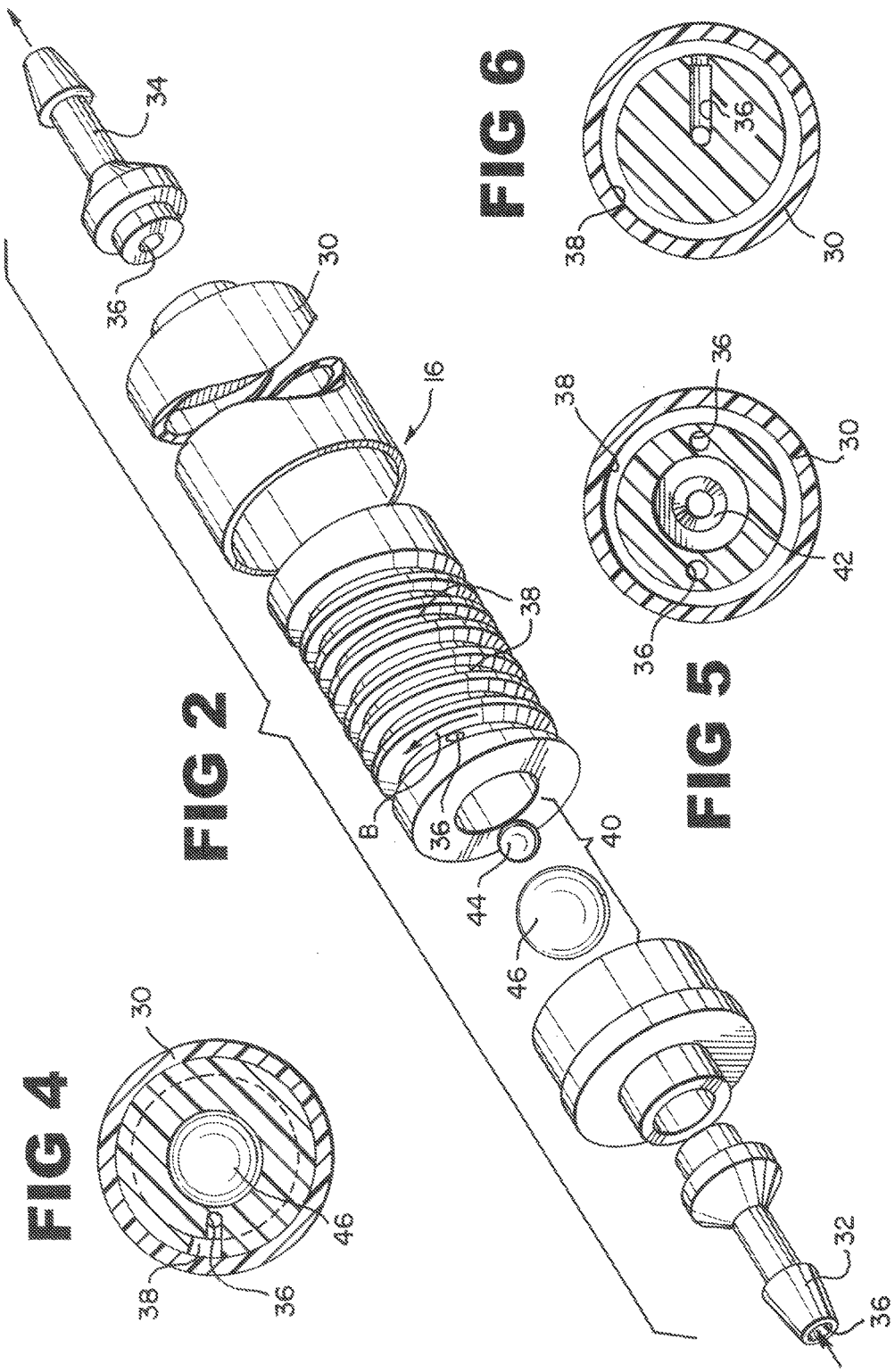

BI-PHASE FLUID SURGE SUPPRESSOR DEVICE

CROSS REFERENCE TO RELATED PCT APPLICATION

This application is a continuation of U.S. patent application Ser. No. 13/799,281, filed Mar. 13, 2013.

BACKGROUND OF THE INVENTION

Field of the Invention

The present invention generally relates to devices used in the treatment of hydrocephalus, and more particularly, to improvements to shunts and siphon control devises used to help divert and regulate excess fluid during the treatment therapy.

Description of the Related Art

The human brain includes four ventricles. Each ventricle contains a choroid plexus that produces cerebrospinal fluid (CSF) which bathes and cushions the brain and spinal cord within their bony and non-elastic confines.

In a normal healthy person, CSF continuously circulates through and around the brain and its ventricles and around the spinal cord and is continuously drained away into the circulatory system so that a controlled pressure is continually maintained within the system. The CSF flows from the lateral ventricles via the foramina of Monro into the third ventricle, and then the fourth ventricle via the cerebral aqueduct in the brainstem. From there it normally can pass into the central canal of the spinal cord or into the cisterns of the subarachnoid space via three small foramina: the central foramen of Magendie and the two lateral foramina of Luschka.

The aqueduct between the third and fourth ventricles is very small, as are the foramina and both are therefore susceptible to becoming blocked or restricted, commonly due to a birth defect, or a local growth, such as that caused by a tumor or infection, thereby disrupting the normal CSF flow. When the CSF flow is impeded, the continued production of CSF will cause an increase in intracranial pressure as the fluid collects within the ventricles.

Alternatively, a similar increase in intracranial pressure of the patient may result from an overproduction of the CSF fluid, from a congenital malformation, or from complications of head injuries or infections, or in some cases, by malabsorption. In any case, the result is the same, an increase of CSF fluid within the ventricles and an increase in intracranial pressure. This condition is called hydrocephalus.

When the CSF accumulates in the cerebral ventricles, the increased volume of fluid compresses the patient's brain tissue since the patient's skull will not yield to this unplanned expansion of fluid. Unfortunately, this compression destroys more and more brain tissue and a variety of secondary symptoms will become apparent in the patient as the neurological functions effectively shut down. These include, headaches, vomiting, dizziness, slurred speech, photophobia/light sensitivity, and in more severe cases, seizures, loss of consciousness and even death.

Hydrocephalus is often treated by the insertion of a diverting catheter into the ventricles of the brain or into the lumbar cistern. Such a catheter or shunt is connected by a regulating valve to a distal catheter which shunts the CSF to another space where it can be reabsorbed and the excess pressure within the brain released. Examples of common diversion sites include the peritoneum of the abdomen via a ventriculoperitoneal shunt or lumboperitoneal shunt or the atrium of the heart via a ventriculoatrial shunt.

A commonly used shunt to treat hydrocephalus is called the Spitz-Holter shunt. It is a conduit that is positioned between the patient's brain and the patient's heart. The device includes a tiny one-way valve that allows a controlled amount of CSF to leave the lateral ventricle of the brain and enter the heart and thereby prevent the increased pressure that causes such damage to the tissues of the brain. This device has helped millions survive this potentially fatal condition since the late 1950s.

About 50% of the shunts fail within the first 5 years after implantation independent of the shunt operating principle and the hydrocephalus etiology. Such shunt failure requires a revision of the shunt system within the patient to avoid a return of original hydrocephalus symptoms. The main causes of failure are infection of the shunt system, obstruction of the shunt, and over-drainage and under-drainage of CSF within the shunt system.

Over-drainage results in an excessive average flow of CFS through the shunt system. This condition may generate an abnormally low intra-cranial pressure, a collapse of the parenchyma and sub-arachnoid hemorrhage.

Some shunt systems use a "Codman® Hakim® valve" or a "Codman® Certas™" programmable valve, which are commercially available from Codman & Shurtleff, Inc. of Raynham, Mass. The Codman® Hakim® and the Codman® Certas™ valve allows a doctor to adjust the valve opening pressure non-invasively after implantation.

Effective fluid flow rate control is particularly important since over-drainage of cerebrospinal fluid can result in dangerous conditions, including subdural hematoma. Over-drainage tends to occur when a patient moves from a horizontal position to a sitting or standing position, due to a siphon effect in the shunt system. To reduce the risk of over-drainage, some shunt systems include additional devices, sometimes referred to as anti-siphon devices, for preventing over-drainage. Some such devices use weights, which move in response to the patient changing position, to open or close the fluid flow path. One system, described in U.S. Pat. No. 5,368,556 (Lecuyer), includes spherical weights which provide additional compressive force against a valve spring to help maintain the valve in a closed position when the patient is sitting or standing. However, noise associated with the use of such weights may be objectionable. Other systems, such as the SIPHONGUARD® Anti-Siphon and Flow-Control Device, as described in U.S. Pat. No. 6,126,628, provides a dual pathway, ball and spring anti-siphon device. The primary pathway is controlled by a ball 110 that is biased by a flat spring bias element 114 and a coil spring counterbias element 112.

For a shunt system with a differential pressure (DP) valve set to 100 mmH$_2$O and connected to a simple gravity actuated valve that requires 200 mmH$_2$O to open in the vertical position. The valve is calibrated to add either 0 mmH$_2$O when horizontal or 200 mmH$_2$O when in the vertical position. Fluid will be driven through the system and into the peritoneal (distal) catheter to drain when the differential pressure exceeds the threshold 100 mmH$_2$O (DP valve setting) in the horizontal position or 300 mmH$_2$O (100 mmH$_2$O valve+200 mmH$_2$O anti-siphon device) when in the vertical position. The anti-siphon device will therefore prevent any fluid drainage until the 300 mmH$_2$O threshold is exceeded.

A drainage problem manifests itself when a patient is not completely vertical (i.e. sleeping on a pillow or bedridden), due to gravity the weighted balls will close off the single fluid pathway and prevent fluid drainage, causing a potentially high increase in the patients ICP such that severe headaches develop, or worse. This will continue until the threshold pressure of 300 mmH$_2$O is exceeded or the anti-siphon device becomes oriented in the horizontal position to open the single fluid pathway.

With the proposed Bi-Phase Fluid Surge Suppressor device, the above drainage problem is mitigated. With a Bi-Phase valve set to 200 mmH$_2$O (in the vertical position), and one has a differential pressure (DP) valve set to 100 mmH$_2$O. When the patient is positioned such that the weighted balls of the Bi-Phase device close the primary pathway, the always open higher resistive secondary pathway allows CSF fluid to drain (when the threshold DP of 100 mmH$_2$O only is exceeded).

Should a patient stand upright (vertical position), the entire system would control the hydrostatic siphoning effect until the threshold of 300 mmH$_2$O (100 mmH$_2$O DP valve+ 200 mmH$_2$O Bi-Phase device) is exceeded. Once exceeded, the Bi-Phase device continues to suppress the surge of fluid until the pressure decreases and the weighted balls seat themselves to close off the primary pathway, while still allowing slow gradual drainage through the secondary pathway until the differential pressure falls below the 100 mmH$_2$O DP valve setting, in this example.

BRIEF DESCRIPTION OF THE DRAWINGS

FIG. 2 is an exploded view of the siphon control device in accordance with the present invention;

FIG. 4 is a cross-sectional view taken along line 4-4 of FIG. 3A and looking in the direction of the arrows;

FIG. 5 is a cross-sectional view taken along line 5-5 of FIG. 3A and looking in the direction of the arrows;

FIG. 6 is a cross-sectional view taken along line 6-6 of FIG. 3A and looking in the direction of the arrows;

DETAILED DESCRIPTION OF THE PRESENT INVENTION

Figure 1:
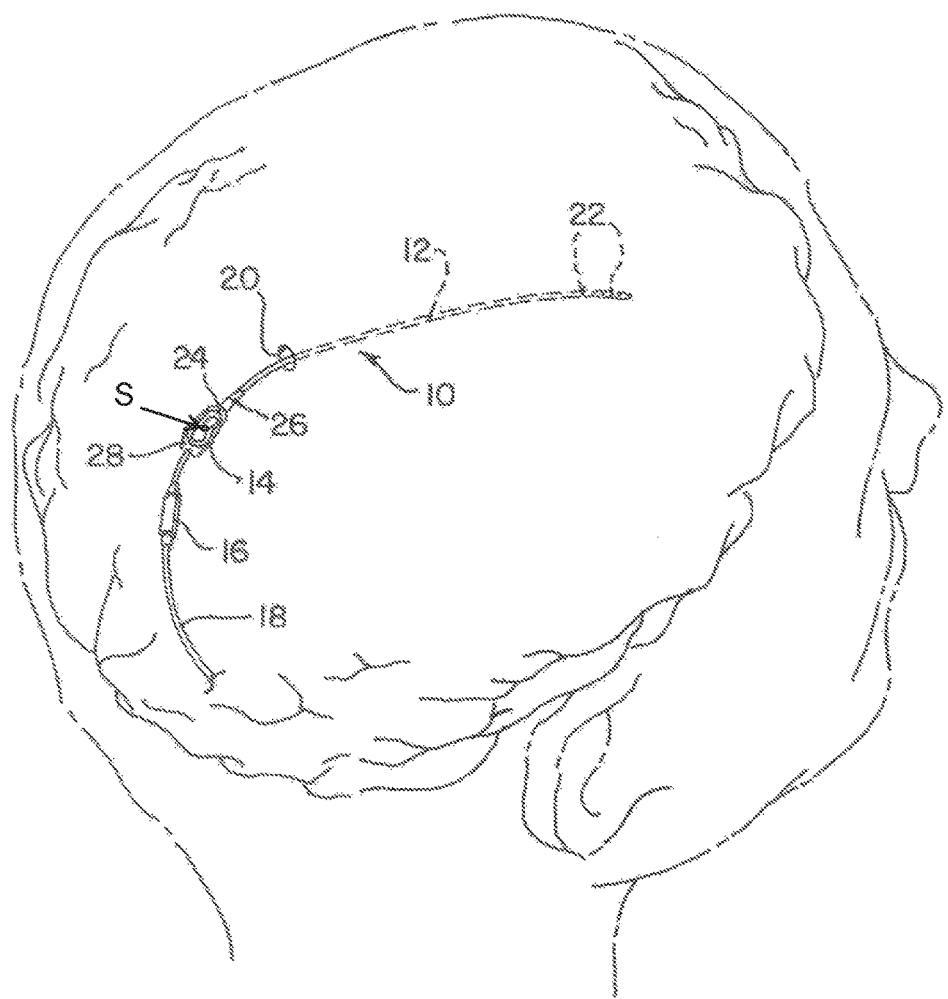
FIG. 1 is a perspective view of view of a shunt system in accordance with the present invention.

Referring now to FIGS. 1-6, a shunt system 10 is illustrated. Shunt system 10 includes a proximal catheter 12, a shunt valve 14, a siphon control device 16 and a distal catheter 18. Proximal catheter 12 is a piece of tubing that is introduced in the ventricle of the brain via a burr hole 20 in the skull as shown in FIG. 1. Proximal catheter 18 has a plurality of through holes 22 at its distal end to permit CSF to enter into the proximal catheter 18 and to be drained from the ventricle. The proximal end of proximal catheter 18 is connected to the housing 24 of shunt valve 14. Housing 24 has an inlet 26 and an outlet 28. A flow path is disposed within the housing 24. A spring biased valve S is disposed within the flow path in the shunt housing 24.

Siphon control device 16 has a second housing 30. Housing 30 has an inlet 32 and an outlet 34. Inlet 32 of siphon control device 16 is in fluid communication with outlet 28 of shunt 14. A primary flow path 36 is disposed within second housing 30 and is in fluid communication with inlet 32 and outlet 34. The primary flow path has a generally axial orientation as shown by arrows A in FIG. 3A. A secondary flow path 38 is disposed within the second housing 30 and is in fluid communication with inlet 32 and outlet 34. Secondary flow path 38 has a generally helical orientation as shown by arrows B in FIGS. 2 and 3B. Secondary flow path 38 has a higher resistance to fluid flow than primary path 36. Secondary flow path 38 is always open.

Figure 3A:
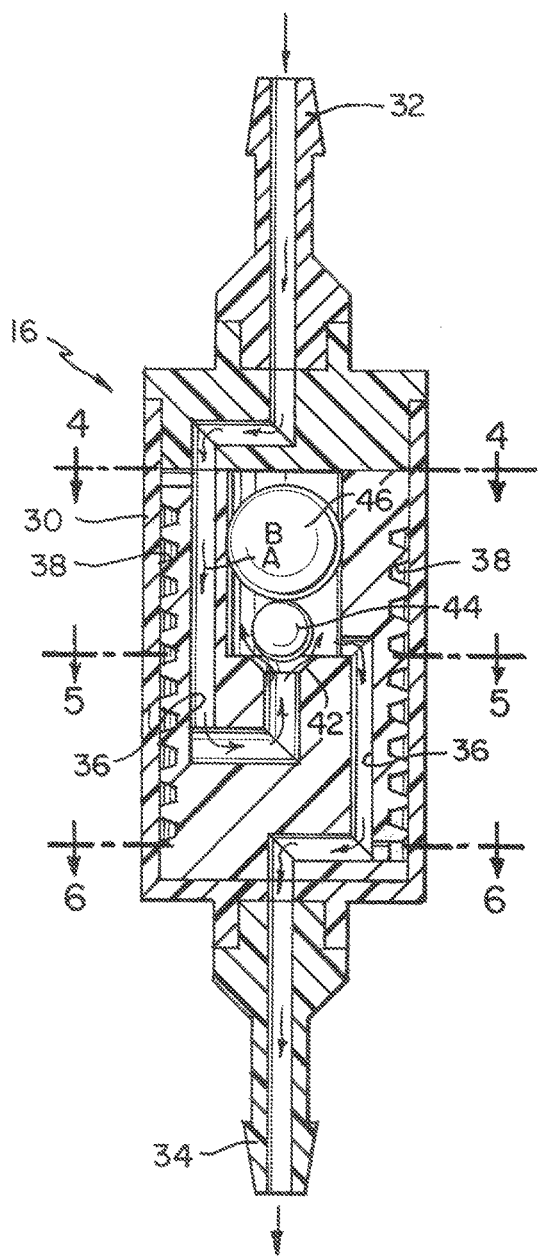
FIG. 3A is a cross-sectional view of the siphon control device in accordance with the present invention showing fluid flowing through both the primary and secondary flow paths.
Figure 3B:
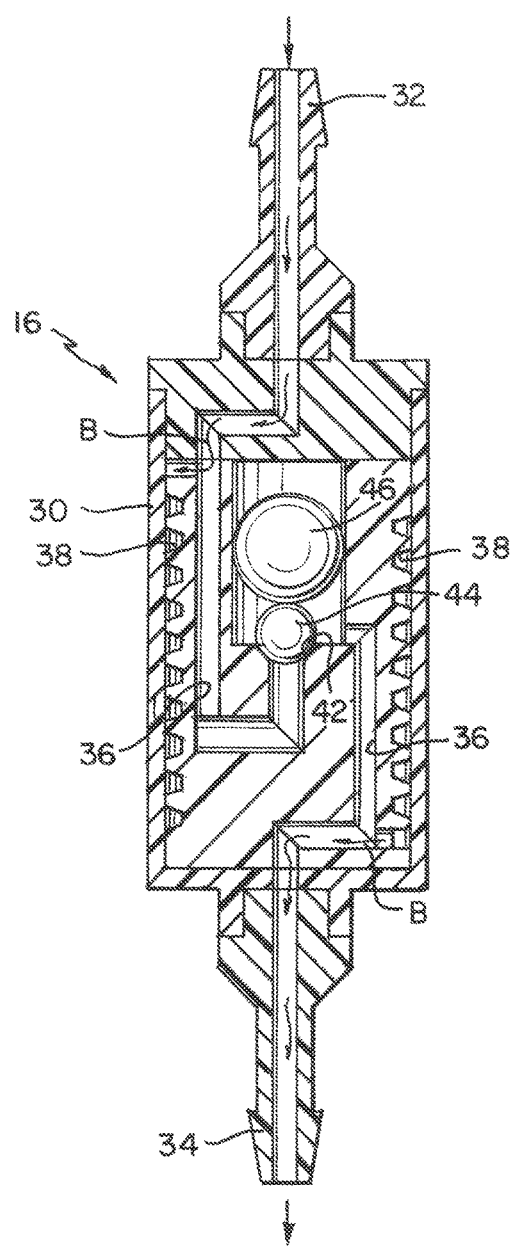
FIG. 3B is a cross-sectional view of the siphon control device in accordance with the present invention showing fluid flowing through only the secondary flow path.
Figure 3C:
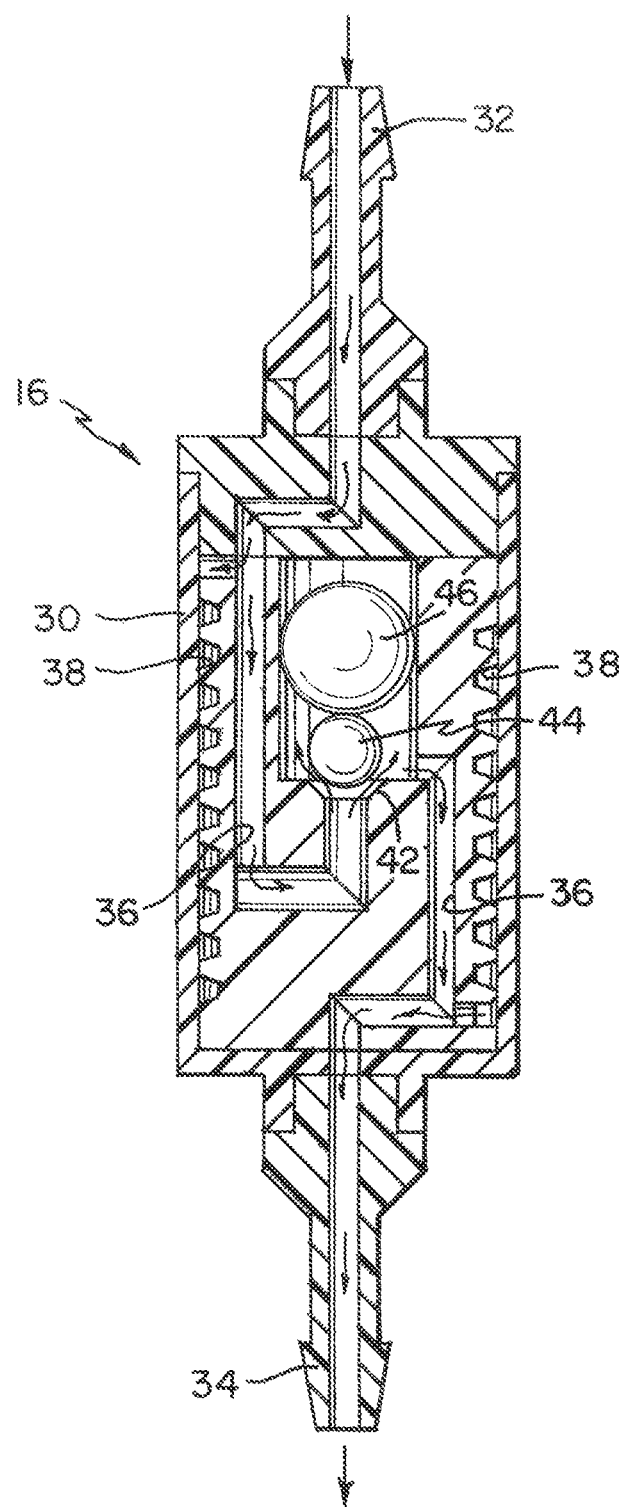
FIG. 3C is a cross-sectional view of the siphon control device in accordance with the present invention showing fluid flowing through both the primary and secondary flow paths.

A valve 40 is disposed within the primary flow path 36. The primary flow path forms a "u" shaped bend between the inlet 26 and the valve 40 (see FIG. 3C). Valve 40 has a valve seat 42 and a first ball 44 and a second ball 46. First ball 44 is movable by gravity between a valve closed position, as shown in FIG. 3B, where the first ball 44 is in contact with valve seat 42, and a valve open position, as shown in FIG. 3A, where the first ball 44 is spaced from valve seat 42. First ball 44 is disposed between the second ball 46 and the valve seat 42. The second ball 46 is also movable by gravity between a valve closed position and a valve open position. Second ball 46 is larger than first ball 44. Second ball 46 preferably weighs more than first ball 44. The first ball 44 and the second ball 46 are biased by gravity. First ball 44 is preferably made of ruby and the second ball is typically made of tantalum metal. Valve seat 42 is also preferably made of ruby.

What is claimed is:

1. A siphon guard comprising:
   a housing having an inlet and an outlet opposite the inlet, the inlet and outlet being axially alignable with a shunt flow path;
   a primary flow path disposed within the housing and in fluid communication with the inlet and the outlet, the primary flow path having a generally axial orientation;
   a secondary flow path disposed around the primary flow path and within the housing and in fluid communication with the inlet and the outlet, the secondary flow path having a generally helical orientation and a higher resistance to fluid flow than the primary path; and
   a valve disposed within the primary flow path, the valve having a valve seat and a first ball and a second ball, the first ball being movable between a valve closed position where the first ball is moved towards the outlet and in contact with the valve seat and a valve open position where the first ball is moved away from the outlet and spaced from the valve seat thereby permitting egress of fluids from the valve from the first ball and then to the outlet distal thereof,
   the first ball is disposed between the second ball and the valve seat,
   the second ball being movable between the valve closed position and the valve open position;
   wherein the second ball being movable by a weight of the second ball between the valve closed position and the valve open position, and
   wherein the primary flow path forms a "u" bend between the inlet and the valve.

2. The siphon guard of claim 1, wherein the second ball is larger than the first ball.

3. The siphon guard of claim 2, wherein the second ball weighs more than the first ball.

4. The siphon guard of claim 1, wherein the first ball is biased by a weight of the first ball and the weight of the second ball.

5. The siphon guard of claim 1, wherein the second flow path is always open.

6. The siphon guard of claim 1, wherein the first ball is made of ruby and the second ball is made of tantalum metal.

7. A shunt and siphon guard kit comprising:
a shunt having a first housing having an inlet and an outlet opposite the inlet, the inlet and outlet being axially alignable with a shunt flow path, a flow path disposed within the first housing;
a spring biased valve being disposed within the flow path in the shunt housing;
a siphon guard having a second housing having an inlet and an outlet, said inlet of the siphon guard being in fluid communication and axially aligned with the outlet of the shunt, a primary flow path disposed within the second housing and in fluid communication with the inlet and the outlet, the primary flow path having a generally axial orientation,
a secondary flow path disposed around the primary flow path and within the second housing and in fluid communication with the inlet and the outlet, the secondary flow path having a generally helical orientation and a higher resistance to fluid flow than the primary path; and
a valve disposed within the primary flow path, the valve having a valve seat and a first ball and a second ball, the first ball being movable between a valve closed position where the first ball is moved towards the outlet and in contact with the valve seat and a valve open position where the first ball is moved away from the outlet and spaced from the valve seat,
the first ball is disposed between the second ball and the valve seat opposite the inlet, the inlet and outlet being axially alignable with a shunt flow path,
wherein the first ball is biased by a weight of the first ball and a weight of the second ball;
wherein the second ball being movable by the weight of the second ball between the valve closed position and the valve open position; and
wherein the primary flow path forms a "u" bend between the inlet and the valve.

8. The siphon guard of claim 7, wherein the second ball is larger than the first ball.

9. The siphon guard of claim 8, wherein the second ball is weighs more than the first ball.

10. The siphon guard of claim 7, wherein the second flow path is always open.

11. The siphon guard of claim 7, wherein the first ball is made of ruby and the second ball is made of tantalum metal.

* * * * *